(12) United States Patent
Yokoyama et al.

(10) Patent No.: US 8,637,112 B2
(45) Date of Patent: Jan. 28, 2014

(54) PROCESS FOR PREDICTING GLOSS OF LOW GLOSS COATING BY WET COLOR MEASUREMENT

(75) Inventors: Ayumu Yokoyama, Wallingford, PA (US); Anthony Moy, Garnet Valley, PA (US)

(73) Assignee: Axalta Coating Systems IP Co., LLC, Wilmington, DE (US)

(*) Notice: Subject to any disclaimer, the term of this patent is extended or adjusted under 35 U.S.C. 154(b) by 0 days.

(21) Appl. No.: 13/191,792

(22) Filed: Jul. 27, 2011

(65) Prior Publication Data

US 2012/0189764 A1  Jul. 26, 2012

Related U.S. Application Data

(60) Provisional application No. 61/393,409, filed on Oct. 15, 2010.

(51) Int. Cl.
*B05D 1/00* (2006.01)
(52) U.S. Cl.
CPC ........................................ *B05D 1/00* (2013.01)
USPC ............................. 427/8; 427/407.1; 427/140
(58) Field of Classification Search
CPC ....................................................... B05D 1/00
USPC .......................................... 427/8, 407.1, 140
See application file for complete search history.

(56) References Cited

U.S. PATENT DOCUMENTS 6,292,264 B1  9/2001  Voye et al.
6,583,878 B2  6/2003  Hustert

FOREIGN PATENT DOCUMENTS

DE              2525701 A1   12/1976

*Primary Examiner* — William Phillip Fletcher, III
(74) *Attorney, Agent, or Firm* — Ingrassia Fisher & Lorenz, P.C.

(57) ABSTRACT

The present invention is directed to a process for process for predicting gloss of a coating resulting from a wet layer of a low gloss coating composition, such as automotive OEM or refinish paint. The process includes measuring reflectance of the layer of the coating composition applied over a test substrate and then allowing the layer to dry and/or cure into a coating. Thereafter, its gloss is measured with a gloss meter. The process is repeated with varying amounts of one or flatting agents added to the composition and the reflectance vs. gloss is plotted on a graph and by using a curve fitting equation a gloss prediction curve is obtained. By measuring the reflectance of a wet layer of a target low gloss coating composition the gloss of a coating that would result from such a layer is then predicted by using the gloss prediction curve. The process is most useful during the manufacture of coating compositions, such as automotive OEM and refinishes paints.

14 Claims, 3 Drawing Sheets

PROCESS FOR PREDICTING GLOSS OF LOW GLOSS COATING BY WET COLOR MEASUREMENT

CROSS-REFERENCE TO RELATED APPLICATION

This application claims priority under 35 U.S.C. §119 from U.S. Provisional Application Ser. No. 61/393,409, filed Oct. 15, 2010, which is hereby incorporated by referenced in its entirety.

FIELD OF INVENTION

The present invention is directed to a process of predicting gloss of a low gloss coating resulting from a layer of a coating composition applied over a substrate. The process is directed to measuring wet color properties of the layer of the coating composition and then predicting the gloss of the coating resulting from the layer applied over a substrate. The process is more particularly directed to a quality assurance process that predicts on a real time basis the gloss of a coating that would result from automotive low gloss OEM and refinish paints while they are being manufactured.

BACKGROUND OF INVENTION

Typically during the manufacturing of coating compositions, such as automotive OEM or refinish paints, from time to time, an aliquot of such coating compositions being manufactured is taken, applied as a layer of desired thickness over a test substrate, dried and/or cured into a coating and it's gloss measured. The process parameters are then adjusted and the aforedescribed testing procedure is repeated until the adjusted coating composition meets the gloss requirements.

The aforementioned testing procedure is not only time consuming and cumbersome but it also results in frequent interruptions in the manufacturing process. As a result, the batch-to-batch quality of the resulting coating compositions can be affected detrimentally. Several methods have been developed to measure optical properties of a layer from a coating composition in its wet state that correlate to the gloss that can result when such a layer dries and/or cures into a coating. However, since the optically proprieties of a wet layer of a coating composition continuously changes due to evaporation of solvent from and/or crosslinking of the wet layer, it becomes difficult to correlate such wet optical property measurements to the gloss of a coating that results from such a layer once it dries and/or cures into a coating. To get around the aforementioned problem, the color properties of a liquid composition stored in a clear glass container could be measured. However, such a solution still does not provide an accurate correlation to what the gloss of the resultant coating would be due to distortions introduced by the reflection and refraction of light beam passing through the walls of the clear glass container. To address the aforedescribed problems, the commonly assigned U.S. Pat. No. 6,292,264 provides for a circulating carrier strip over which a layer of coating composition is applied and then its optical properties are measured by a non-contact optical device soon after the layer is cast over the carrier strip as it passes underneath the optical device. However, the need still exists to develop a process that correlates the optical properties of a wet layer of a low gloss coating composition containing flatting agent to predicting the gloss of the coating resulting from such a layer.

STATEMENT OF INVENTION

The present invention is directed to a gloss prediction process comprising:

(a) dispensing on a test substrate a $L_0$ layer of a substantially uniform thickness of a coating composition through a vessel of a gloss prediction device containing said coating composition;

(b) projecting on said $L_0$ layer a beam of light of a preset intensity at a preset angle of incidence from a light source;

(c) measuring $B_0$ reflectance of said beam reflected from said $L_0$ layer at a preset angle of reflectance by an optical measurement instrument;

(d) curing or drying said $L_0$ layer into a $C_0$ coating;

(e) measuring $Y_0$ gloss of said $C_0$ coating at a preset gloss angle by a gloss meter;

(f) storing said $B_0$ reflectance of said $L_0$ layer and said $Y_0$ gloss of said $C_0$ coating in a computer usable storage medium of a computer;

(g) repeating said steps (a) through (f) for $S_1$ to $S_n$ coating compositions respectively comprising $F_1$ to $F_n$ parts by weight of one or more flatting agents based on 100 parts by weight of said coating composition to determine $B_1$ to $B_n$ reflectance of $L_1$ to $L_n$ layers and $Y_1$ to $Y_n$ gloss of $C_1$ to $C_n$ coatings wherein n ranges from 4 to 20;

(h) subtracting said $B_0$ reflectance of said $L_0$ layer from said $B_1$ to $B_n$ reflectance of said $L_1$ to $L_n$ layers to determine $\Delta B_1$ to $\Delta B_n$ of said $L_1$ to $L_n$ layers respectively;

(i) locating intersecting points on a graph where said $\Delta B_1$ to $\Delta B_n$ of said $L_1$ to $L_n$ layers on X-axis of said graph intersect with said $Y_1$ to $Y_n$ gloss of said $C_1$ to $C_n$ coatings on Y-axis of said graph;

(j) using a curve fitting equation to produce a gloss prediction curve on said graph;

(k) dispensing on said test substrate a $L_T$ layer of said substantially uniform thickness of a target coating composition through said vessel of said wet gloss prediction device containing said target coating composition further comprising said flatting agent;

(l) projecting on said $L_T$ layer a beam of light at said preset intensity and at said preset angle of incidence from said light source;

(m) measuring $B_T$ reflectance of said beam reflected from said $L_T$ layer at said preset angle of reflectance by said optical measurement device;

(n) subtracting said $B_0$ of said $L_0$ layer from said $B_T$ of $L_T$ layer to determine $\Delta B_T$ of said $L_T$ layer;

(o) locating said $\Delta B_T$ of said $L_T$ layer on said X-axis of said graph;

(n) locating an intersecting point on said gloss prediction curve that intersects with said $\Delta B_T$ on said X-axis of said graph; and (p) predicting gloss at said preset gloss angle of a target coating resulting from said target layer by locating $Y_T$ on said Y-axis of said graph that intersects with said intersecting point on said gloss prediction curve that intersects with said $\Delta B_T$ on said X-axis of said graph.

DETAILED DESCRIPTION OF PREFERRED THE EMBODIMENT

As defined herein:

"Low gloss coating composition" means a coating composition that contains one or more flatting agents that reduce the gloss of a coating resulting from a layer of such a coating composition applied over a substrate, such as an automotive body, bumper or a fender. The higher the amount of the flatting agent in the coating composition, the lower will be the gloss of a coating resulting therefrom and vice versa. Typical flatting agents include talc, silica, or barium sulfate or a combination thereof that produce coatings having satin, flat or semi-gloss finish.

Figure 1:
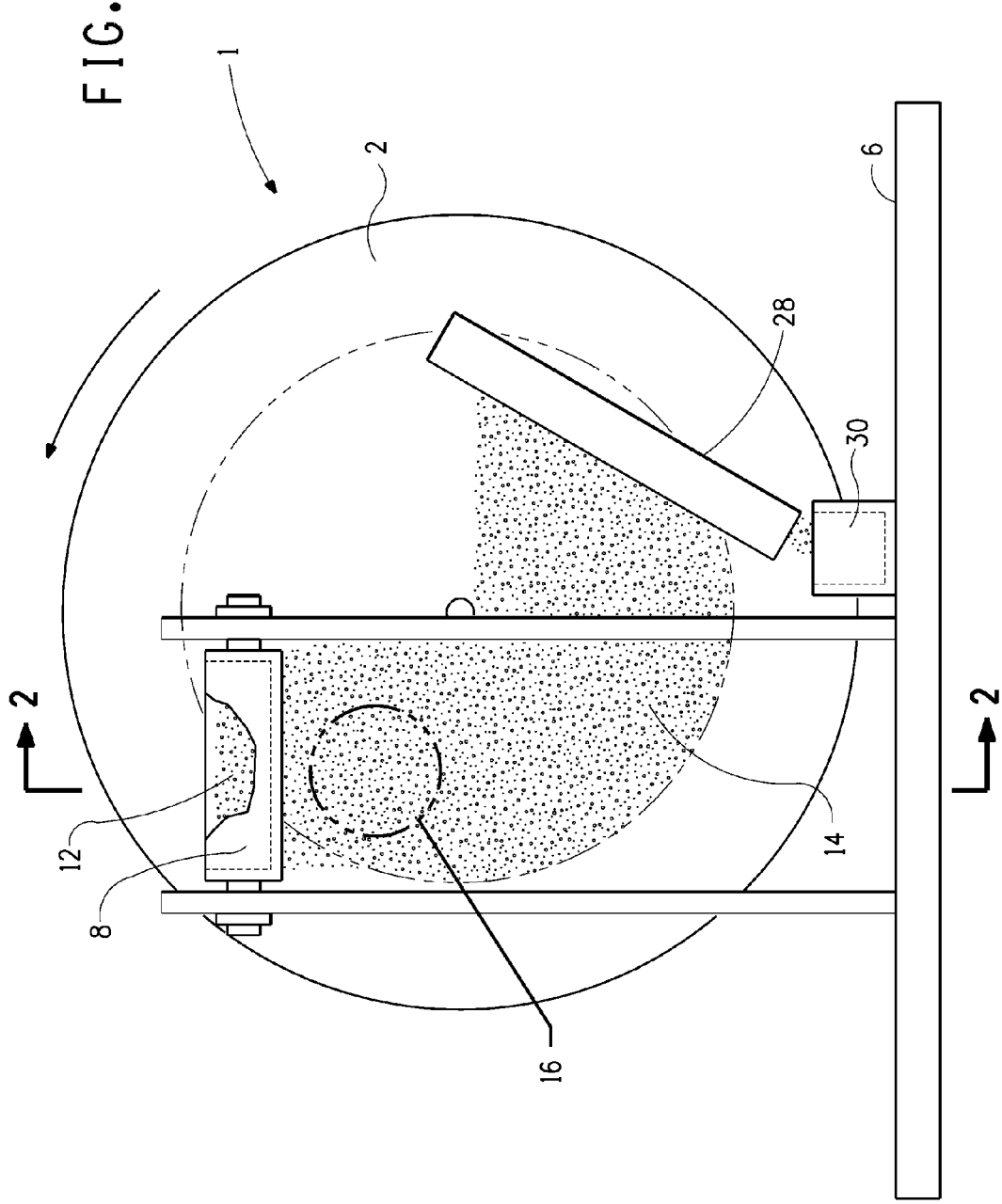
FIGS. 1 and 2 broadly illustrate one of the embodiments of a gloss prediction device of the present invention.
Figure 2:
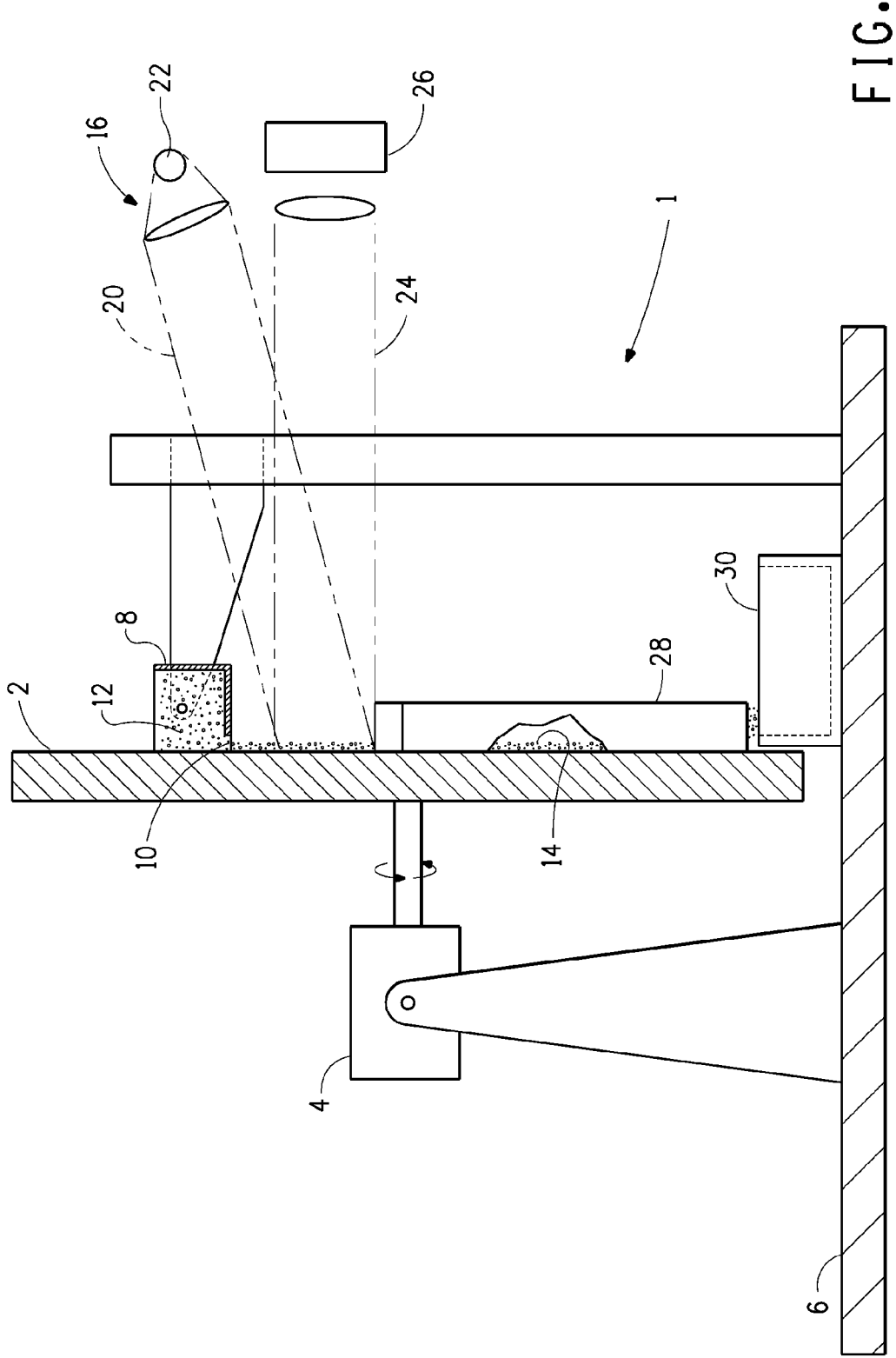
Figure 3:
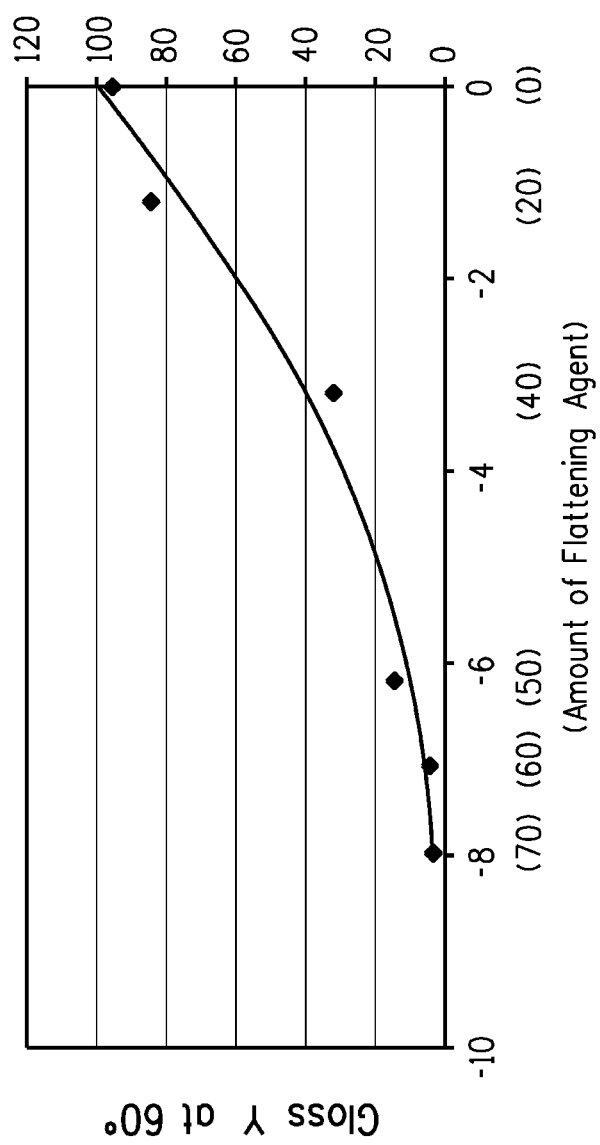
FIG. 3 broadly illustrates the gloss prediction curve produced by the gloss prediction device of the present invention.

One of the gloss prediction devices suitable for the process of the present invention includes a device 1 shown in FIGS. 1 and 2. Device 1 includes a test substrate 2, preferably a disc, rotated by a driver 4, such as an electric motor, which is positioned on a support frame 6. Test substrate 2 mounted on a shaft of driver 4 can be positioned either in a horizontal or in a vertical position. Test substrate 2 of device 2 shown in FIGS. 1 and 2 is positioned vertically, which is preferred. Test substrate 2 can be made of any suitable material, such as steel, plastic or aluminum. The surface of test substrate 2 preferably has the same degree of smoothness as that of, for example, auto body or auto bumper such that the results obtained are as close to those that would have been obtained under the similar paint application conditions.

As shown in FIG. 1, Device 1 is provided with a vessel 8 positioned adjacent to test substrate 2. Vessel 8 is provided with an opening 10, preferably a slot, through which a coating composition 12, when poured into vessel 8, can be applied as a $L_0$ layer 14 of a substantially uniform thickness on a measurement area 16 on the surface of test substrate 2. Coating composition 12 used in producing $L_0$ layer 14 is free from any flatting agent. As test substrate 2 is rotated by driver 4, preferably for about a quarter turn, $L_0$ layer 14 is created. Opening 10 is adjacent to substrate 2 such that a resulting gap between opening 10 and substrate 2 controls the thickness of $L_0$ layer. Typically, $L_0$ layer is provided with a thickness that ranges from 6 micrometers to 2300 micrometers.

Device 2 includes a conventional optical measurement mechanism 16 provided with conventional collimators for producing a beam of light 20 of preset intensity at a preset angle that can be projected on measurement area 16 from a conventional light source 22. A $B_0$ reflectance 24 of beam of light 20 off of $L_0$ layer 14 can then be measured by a conventional optical measurement instrument 26. A conventional optical measurement instrument typically measures conventional L,a,b color data on the reflectance of a surface color wherein L factor refers to lightness or darkness, "a" factor refers to (+a) redness to greenness (−a) and "b" factor refers to (+b) yellowness to blueness (−b). The applicants have unexpectedly discovered that the use of data from "b" factor reported as ("B reflectance" above) results in the closest curve fitting of the data. Any angle of incidence and reflectance can be used. However, a 60 degree angle of reflectance is typically employed and is preferably measured before there is substantial change in the optical characteristics of $L_0$ layer 14 that depend on the physical and chemical properties of the coating composition from which $L_0$ layer 14 is produced. Thus, the higher the content of the solvent in the coating composition, the longer would be the window during which the reflectance can be measured and vice versa. Coating compositions that are lacquers (those containing high molecular weight non-reactive binder polymers dissolved in a solvent) typically would have longer measurement window than coating compositions that are enamels (those containing binder polymers containing reactive groups that chemically react with crosslinking groups on crosslinking agents that are mixed before being applied as a layer on a substrate). Typically, the reflectance is measured within 2 seconds to two minutes after $L_0$ layer 14 is applied over test substrate 2.

After the measurement of reflectance, $L_0$ layer 14 is allowed to dry and/or cure into a $C_0$ coating and its $Y_0$ gloss is measured by means of a gloss meter (not-shown in FIG. 1) at a preset gloss angle, which is preferably 60 degrees. Generally, gloss is measured within 15 seconds to 3 hours, preferably within 30 seconds to an hour, after coating composition 12 is applied over substrate 2. Means for configuring computer readable program code devices is used to cause a conventional computer to store $B_0$ reflectance 24 of $L_0$ layer 14 and $Y_0$ gloss in a computer usable storage medium of the computer (not-shown in FIG. 1). The computer is preferably in communication with optical measurement instrument 26 and the gloss meter. If desired, the computer can be in communication with a remote computer, such as an offsite computer used to gather information from one or more computers connected to gloss prediction devices of the present invention.

If desired, after $Y_0$ gloss of $C_0$ coating is measured, substrate 2 can be rotated further by driver 4 to scrape off $C_0$ coating with a doctor blade 28 into a waste container 30 and substrate 2 can then be cleaned. Alternatively, after $Y_0$ gloss of $C_0$ coating is measured, substrate 2 can be removed and $C_0$ coating scraped off substrate 2 and then cleaned.

The aforedescribed procedure is then repeated with series of $S_1, S_2, \ldots S_n$ (n being in the range of 4 to 20) coating compositions 12 containing increasing amounts one or more flatting agents ranging from $F_1$ to $F_n$ weight parts per 100 weight parts of coating composition. The amount of flatting agent added to the coating composition can be increased in set amounts, such as 5, 10, 15 weight parts in per 100 weight parts of the coating composition, with $F_1$ ranging from 1 weight part to 10 weight parts per 100 weight parts of the coating composition and $F_n$ ranging from 40 weight parts to 100 weight parts per 100 weight parts of coating composition. As described above, $B_1$ reflectance 24 from a $L_1$ layer 14 from $S_1$ coating composition and $Y_1$ gloss of a $C_1$ coating that results from curing $L_1$ layer 14 into $C_1$ coating is measured and the means for configuring computer readable program code devices is used to cause the computer to store $B_1$ reflectance 24 of $L_1$ layer 14 and $Y_1$ gloss in the computer usable storage medium of the computer. The process is repeated till $B_n$ reflectance from a $L_n$ layer 14 from coating composition $12_n$ and $Y_n$ gloss of a $C_n$ coating that results from curing $L_n$ layer 14 into $C_n$ coating is measured and stored in the computer usable storage medium of the computer.

The means for configuring computer readable program code devices is used to cause the computer to subtract $B_0$ reflectance 24 from each of $B_1$ to Bn reflectance 24 to determine $\Delta B_1$ to $\Delta B_n$ of $L_1$ to $L_n$ layers 14, which are then stored in the computer usable storage medium of the computer.

The means for configuring computer readable program code devices is used to cause the computer to locate intersecting points on a graph where $\Delta B_1$ to $\Delta B_n$ of $L_1$ to $L_n$ layers 14 on X-axis of the graph intersect with the $Y_1$ to $Y_n$ gloss of the $C_1$ to $C_n$ coatings on Y-axis of the graph. The means for configuring computer readable program code devices is then used to cause the computer to use a curve fitting equation to produce a gloss prediction curve on the graph. Preferably, the curve fitting equation is a second degree polynomial equation. More preferred second degree polynomial equation is of the following formula:

$$\text{Gloss } Y = a(\Delta B_n)^2 + b(\Delta B_n) + c \tag{1}$$

$$R^2 = Z \tag{2}$$

wherein said constants a, b, c and $R^2$ are determined by a curve fitting process, such as that described in Microsoft Office Excel® 2003 supplied by Microsoft Corporation of Redmond, Wash. Z is a statistical measure of how close the curve fits to the experimental datum points on a graph. When Z is equal to 1, it is considered to be an ideal fit, i.e., all the experimental datum points lay on the fit curve. All the necessary and relevant information is stored on the computer usable storage medium.

If desired, the gloss prediction curve on the graph may be displayed on a conventional monitor and/or printed on paper by means of a conventional printer both of which being in communication with the computer. Once the gloss prediction curve on the graph is produced, the user can use the wet gloss prediction device of the present invention to predict the gloss of a target coating composition containing an unknown or known amount of one or more flatting agents without going through the cumbersome and time consuming process of curing the layer into a coating. $L_T$ layer 14 (also know as target layer) from the target coating composition, preferably having the same substantially uniform thickness as the layers used in creating the gloss prediction curve, dispensed over substrate 2 of wet gloss prediction device 1 of the present invention can be used in a production set up that allows the manufacturer of a coating composition to expeditiously adjust the ingredients of the coating composition for ensuring that the resulting coating composition has a desired gloss.

As described above, $B_T$ reflectance 24 from $L_T$ layer 14 from the target coating composition is measured and the means for configuring computer readable program code devices is used to cause the computer to store $B_T$ reflectance 24 of $L_T$ layer 14 in the computer usable storage medium of the computer. The means for configuring computer readable program code devices is used to then cause the computer to subtract $B_0$ reflectance of $L_0$ layer from $B_T$ reflectance of $L_T$ layer to determine $\Delta B_T$ of $L_T$ layer.

The means for configuring computer readable program code devices is used to cause the computer to locate $\Delta B_T$ of $L_T$ layer on the X-axis of the graph. The means for configuring computer readable program code devices is used to cause the computer to locate an intersecting point on the gloss prediction curve that intersects with $\Delta B_T$ on X-axis of the graph. Finally, The means for configuring computer readable program code devices is used to cause the computer to predict gloss of a target coating resulting from $L_T$ layer by locating $Y_T$ gloss on the Y-axis of the graph that intersects with the intersecting point on the gloss prediction curve that intersects with $\Delta B_T$ on the X-axis of the graph.

Few of the aspects of the aforedescribed gloss prediction device 1 of the present invention are described in German patent application DT 25 25 701 A1. It should be understood that substrate 2 need not be positioned vertically or have to have a disc shape. Other embodiments, such as those where substrate is positioned horizontally, or is in the form of a belt, etc. are also well suited for the process of the present invention. For example, substrate in the form of a roller, as described in a commonly assigned U.S. Pat. No. 6,583,878 to Hustert, is also well suited for the process of the present invention.

The process of the present invention utilizes gloss prediction device 1 of FIG. 1. The process includes dispensing on substrate 2, $L_0$ layer 14 of a substantially uniform thickness of coating composition 12 through vessel 8, which contains containing coating composition 12. Then beam of light 20 of a preset intensity at a preset angle of incidence from light source 22 is projected on measurement area 16 of $L_0$ layer. By means of optical measurement instrument 26, $B_0$ reflectance of beam of light 20 is measured a preset angle of reflectance. $L_0$ layer is dried and/or cured into $C_0$ coating and $Y_0$ gloss of $C_0$ coating at a preset gloss angle by gloss meter at a preset gloss angle. $B_0$ reflectance of $L_0$ layer and $Y_0$ gloss of $C_0$ coating is then stored in the computer usable storage medium of the computer. The aforedescribed steps are repeated for $S_1$ to $S_n$ coating compositions 12 further comprising $F_1$ to $F_n$ parts by weight of one or more flatting agents based on 100 parts by weight of the coating composition respectively to determine $B_1$ to $B_n$ reflectance of $L_1$ to $L_n$ layers and $Y_1$ to $Y_n$ gloss of $C_1$ to $C_n$ coatings wherein n ranges from 4 to 20. $B_0$ reflectance of $L_0$ layer is then subtracted from $B_1$ to $B_n$ reflectance of $L_1$ to $L_n$ layers to determine $\Delta B_1$ to $\Delta B_n$ of $L_1$ to $L_n$ layers respectively.

EXAMPLES

Table 1 below shows one example of a two-pack enamel (coating composition) in which increasing amounts of flatting agent (fumed silica) were added and then resulting $\Delta$Bs were reported.

TABLE 1

| P | Q | b | $\Delta$b | Y |
|---|---|---|---|---|
| 100 | 0 | 52.66 | 0 | 95 |
| 80 | 20 | | −1.34 | 85 |
| 60 | 40 | | −3.28 | 30 |
| 50 | 50 | | −6.18 | 15 |
| 40 | 60 | | −7.03 | 5 |
| 30 | 70 | | −7.93 | 3 |

P is coating composition in grams (DuPont EcoMax ™ Topcoat TU09-3001 activated with DuPont EcoMax ™ Activator TU-09AS, both supplied by DuPont Company of Wilmington, Delaware).
Q is DuPont Industrial Strength Flattener 9T20 flatting agent in grams supplied by DuPont Company of Wilmington, Delaware.
b data relates to reflectance of a layer of the coating composition containing the flatting agents in the amounts shown.
Y is gloss measured from coatings resulting from the cured layers of the coating composition containing the flatting agents in the amounts shown.

As shown in FIG. 2, intersecting points on a graph where $\Delta B_1$ to $\Delta B_n$ of $L_1$ to $L_n$ layers on X-axis of the graph intersect with $Y_1$ to $Y_n$ gloss of $C_1$ to $C_n$ coatings on Y-axis of the graph are then located.

Using a curve fitting equation, such as the aforementioned secondary degree polynomial equation (1) is then used to produce a gloss prediction curve, such as that shown in FIG. 2. The term "a" in the equation (1) was 1.3319. The term "b" in the equation (1) was 22.791 and the term "c" in the equation was 100.49. The statistical measure Z was 0.9625. All the of the foregoing terms were obtained by using the aforementioned Microsoft Excel® program. It would be readily to apparent to one of ordinary skill in the art that the statistical measure Z of 0.9625 indicates the curve of the gloss prediction was very close fit to the Z of the ideal fit of 1. The foregoing is also confirmed from Table 2 below, which shows the gloss predicted by the gloss prediction curve and the actual gloss measured. Thus, one of ordinary skill in the art can readily see from Table 2 that the gloss predicted by the gloss prediction curve by the process and the device of the present invention comes substantially close to the actual gloss of the resultant coatings that was measured by means of the gloss meter.

TABLE 2

| Q | Predicted Y | Measured Y |
|---|---|---|
| 0 | 100 | 95 |
| 20 | 78 | 85 |
| 40 | 40 | 30 |
| 50 | 12 | 15 |

TABLE 2-continued

| Q  | Predicted Y | Measured Y |
|----|-------------|------------|
| 60 | 6           | 5          |
| 70 | 3           | 3          |

Q amount of flatting agent in grams.
Y gloss.

The process of the present invention is then used to predict the gloss of a target coating composition by first dispensing on substrate 2 a $L_T$ layer of preferably the same substantially uniform thickness of a target coating composition through vessel 8 of wet gloss prediction device 1 containing the target coating composition further comprising an unknown or a known amount of the flatting agent. A beam of light 20 at the preset intensity and at the preset angle of incidence from light source 22 is then projected on measurement area 16 of $L_T$ layer and $B_T$ reflectance of beam reflected from $L_T$ layer at the preset angle of reflectance is measured by optical measurement instrument 26. $B_0$ of $L_0$ layer is then subtracted from $B_T$ of $L_T$ layer to determine $\Delta B_T$ of $L_T$ layer, which is then located on the X-axis of the graph. An intersecting point on the gloss prediction curve that intersects with $\Delta B_T$ on the X-axis of said graph is then located and gloss at the preset gloss angle of a coating resulting from $L_T$ layer is then predicted by locating $Y_T$ on the Y-axis of the graph.

The process and device of the present invention is most suitable for predicting the gloss of automotive OEM and refinish paints during their. However, it is also well suited for architectural coatings or any other coatings made from low gloss coating compositions.

What is claimed is:

1. A gloss prediction process comprising:
   (a) dispensing on a test substrate a $L_0$ layer of a substantially uniform thickness of a coating composition through a vessel of a gloss prediction device containing said coating composition, wherein said thickness is controlled by a gap between a slot provided on said vessel and said substrate;
   (b) projecting on said $L_0$ layer a beam of light of a preset intensity at a preset angle of incidence from a light source;
   (c) measuring $B_0$ reflectance of said beam reflected from said $L_0$ layer at a preset angle of reflectance by an optical measurement instrument;
   (d) curing or drying said $L_0$ layer into a $C_0$ coating;
   (e) measuring $Y_0$ gloss of said $C_0$ coating at a preset gloss angle by a gloss meter;
   (f) storing said $B_0$ reflectance of said $L_0$ layer and said $Y_0$ gloss of said $C_0$ coating in a computer usable storage medium of a computer;
   (g) repeating said steps (a) through (f) for $S_1$ to $S_n$ coating compositions respectively comprising $F_1$ to $F_n$ parts by weight of one or more flatting agents based on 100 parts by weight of said coating composition to determine $B_1$ to $B_n$ reflectance of $L_1$ to $L_n$ layers and $Y_1$ to $Y_n$ gloss of $C_1$ to $C_n$ coatings wherein n ranges from 4 to 20;
   (h) subtracting said $B_0$ reflectance of said $L_0$ layer from said $B_1$ to $B_n$ reflectance of said $L_1$ to $L_n$ layers to determine $\Delta B_1$ to $\Delta B_n$ of said $L_1$ to $L_n$ layers respectively;
   (i) locating intersecting points on a graph where said $\Delta B_1$ to $\Delta B_n$ of said $L_1$ to $L_n$ layers on X-axis of said graph intersect with said $Y_1$ to $Y_n$ gloss of said $C_1$ to $C_n$ coatings on Y-axis of said graph;
   (j) using a curve fitting equation to produce a gloss prediction curve on said graph;
   (k) dispensing on said test substrate a $L_T$ layer of said substantially uniform thickness of a target coating composition through said vessel of said wet gloss prediction device containing said target coating composition further comprising said flatting agent;
   (l) projecting on said $L_T$ layer a beam of light at said preset intensity and at said preset angle of incidence from said light source;
   (m) measuring $B_T$ reflectance of said beam reflected from said $L_T$ layer at said preset angle of reflectance by said optical measurement device;
   (n) subtracting said $B_0$ of said $L_0$ layer from said $B_T$ of $L_T$ layer to determine $\Delta B_T$ of said $L_T$ layer;
   (o) locating said $\Delta B_T$ of said $L_T$ layer on said X-axis of said graph;
   (n) locating an intersecting point on said gloss prediction curve that intersects with said $\Delta B_T$ on said X-axis of said graph; and
   (p) predicting gloss at said preset gloss angle of a target coating resulting from said target layer by locating $Y_T$ on said Y-axis of said graph that intersects with said intersecting point on said gloss prediction curve that intersects with said $\Delta B_T$ on said X-axis of said graph.

2. The process of claim 1 wherein said optical measurement device is a spectrophotometer.

3. The process of claim 1 wherein said optical measurement instrument is in communication with said computer.

4. The process of claim 1 wherein said gloss meter is in communication with said computer.

5. The process of claim 1 wherein said opening is a slot adjacent to said test substrate such that a resulting gap between said slot and said test substrate controls the thickness of said $L_0$ and said $L_1$ to $L_n$ layers.

6. The process of claim 1 wherein said $L_0$ and said $L_1$ to $L_n$ layers are of the same thickness ranging from 6 micrometers to 2300 micrometers.

7. The process of claim 1 wherein said test substrate is a disc positioned substantially vertically on a support frame of said gloss prediction device.

8. The process of claim 1 wherein said curve fitting equation is a second degree polynomial equation.

9. The process of claim 8 wherein said second degree polynomial equation is of the formula:

$$\text{Gloss } Y = a(\Delta B_n)^2 + b(\Delta B_n) + c$$

$$R^2 = Z$$

wherein said constants a, b, c and Z are determined by a curve fitting process.

10. The process of claim 1 comprising displaying said predicted gloss of said target coating on a CRT monitor.

11. The process of claim 1 comprising communicating said predicted gloss of said target coating from said computer to a remote computer.

12. The process of claim 1 wherein said coating composition is an automotive OEM or refinish paint.

13. The process of claim 12 wherein said flatting agent is talc, silica, or barium sulfate.

14. The process of claim 13 wherein said $F_1$ is 10 parts and said $F_n$ is 90 parts by weight of one or more flatting agents based on 100 parts by weight of said coating composition.

* * * * *